United States Patent
Tsukashima et al.

(10) Patent No.: US 7,297,120 B2
(45) Date of Patent: Nov. 20, 2007

(54) RESPIRATORY MONITORING, DIAGNOSTIC AND THERAPEUTIC SYSTEM

(75) Inventors: Ross Tsukashima, San Diego, CA (US); Jeffery D. Schipper, Ramona, CA (US); Leo R. Roucher, Jr., Rancho Santa Fe, CA (US); Erich H. Wolf, Vista, CA (US)

(73) Assignee: Sierra Medical Technology, Inc., San Diego, CA (US)

( * ) Notice: Subject to any disclaimer, the term of this patent is extended or adjusted under 35 U.S.C. 154(b) by 836 days.

(21) Appl. No.: 10/693,115

(22) Filed: Oct. 24, 2003

(65) Prior Publication Data

US 2004/0210153 A1 Oct. 21, 2004

Related U.S. Application Data

(63) Continuation-in-part of application No. 10/413,701, filed on Apr. 15, 2003, now Pat. No. 7,101,341.

(51) Int. Cl.
*A61B 5/05* (2006.01)
*G01N 1/22* (2006.01)
*G01N 31/00* (2006.01)
*G01N 33/497* (2006.01)
*B32B 5/02* (2006.01)
*B32B 27/04* (2006.01)
*B32B 27/12* (2006.01)

(52) U.S. Cl. .................. 600/532; 73/23.3; 422/84
(58) Field of Classification Search ............ None
See application file for complete search history.

(56) References Cited

U.S. PATENT DOCUMENTS

| | | | |
|---|---|---|---|
| 3,946,726 A | 3/1976 | Pikui | |
| 3,991,304 A | 11/1976 | Hillsman | |
| 4,366,821 A | 1/1983 | Wittmaier et al. | |
| 5,042,501 A | 8/1991 | Kenny et al. | |
| 5,069,220 A | 12/1991 | Casparie et al. | |
| 5,081,871 A | 1/1992 | Glaser | |
| 5,140,993 A | 8/1992 | Opekun, Jr. et al. | |
| 5,174,959 A | 12/1992 | Kundu et al. | |
| 5,213,109 A | 5/1993 | Susi | |
| 5,265,595 A | 11/1993 | Rudolph | |
| 5,327,901 A | 7/1994 | Delente | |
| 5,361,772 A | 11/1994 | Murnick et al. | |
| 5,432,094 A | 7/1995 | Delente | |
| 5,465,728 A | 11/1995 | Philips | |
| 5,645,049 A | 7/1997 | Foley et al. | |
| 5,676,154 A | 10/1997 | Pettersson | |
| 5,795,787 A | 8/1998 | Silkoff et al. | |
| 5,826,577 A | 10/1998 | Perroz, Jr. et al. | |

(Continued)

*Primary Examiner*—Robert Nasser, Jr.
(74) *Attorney, Agent, or Firm*—Michael Klicpera (57) ABSTRACT

Disclosed is a system and method for monitoring, diagnosing, and treating certain medical conditions, such as asthma, gastroesophageal reflux or laryngopharyngeal reflux. The system includes a mask apparatus or sensor module fitted with a pH sensor and thermocouple, a continuous positive airway pressure (CPAP) device, a processing receiver, and a therapeutic nebulizer/atomizer/humidifier device. The mask apparatus, CPAP device and therapeutic nebulizer/atomizer/humidifier device are connected by a pneumatic means. The pH sensor and the thermocouple are in electrical communication with the processing receiver that controls, through an electronic means, the CPAP device and therapeutic nebulizer/atomizer/humidifier device. The electrical communications can be in the form of a plurality of wires or employ wireless means.

31 Claims, 7 Drawing Sheets

U.S. PATENT DOCUMENTS

| | | |
|---|---|---|
| 5,857,460 A | 1/1999 | Popitz |
| 5,922,610 A | 7/1999 | Alving et al. |
| 5,962,335 A | 10/1999 | Katzman |
| 6,010,459 A | 1/2000 | Silkoff et al. |
| 6,033,368 A | 3/2000 | Gaston, IV et al. |
| 6,053,874 A | 4/2000 | Kharitonov et al. |
| 6,067,983 A | 5/2000 | Stenzler |
| 6,180,414 B1 | 1/2001 | Katzman |
| 6,186,958 B1 | 2/2001 | Katzman et al. |
| 6,213,955 B1 | 4/2001 | Karakasoglu et al. |
| 6,221,026 B1 | 4/2001 | Philips |
| 6,312,390 B1 | 11/2001 | Philips |
| 6,398,739 B1 | 6/2002 | Sullivan et al. |
| 6,419,634 B1 | 7/2002 | Gaston, IV et al. |
| 6,479,019 B1 | 11/2002 | Goldstein et al. |
| 6,491,643 B2 | 12/2002 | Katzman et al. |
| 6,540,691 B1 | 4/2003 | Philips |
| 6,582,376 B2 | 6/2003 | Baghdassarian |
| 6,585,661 B1 | 7/2003 | Hunt et al. |
| 6,599,253 B1 | 7/2003 | Baum et al. |
| 6,612,306 B1 | 9/2003 | Mault |
| 2003/0013695 A1 | 1/2003 | Hunt et al. |
| 2003/0023181 A1* | 1/2003 | Mault ......................... 600/532 |
| 2003/0023389 A1 | 1/2003 | Rothe et al. |
| 2003/0134427 A1 | 7/2003 | Roller et al. |
| 2003/0208133 A1* | 11/2003 | Mault ......................... 600/532 |

* cited by examiner

RESPIRATORY MONITORING, DIAGNOSTIC AND THERAPEUTIC SYSTEM

CROSS-REFERENCES

The present application is a continuation-in-part of application Ser. No. 10/413,701 filed on Apr. 15, 2003 entitled "A Respiratory Monitoring, Diagnostic and Therapeutic System" now U.S. Pat. No. 7,101,341. This application is incorporated herein by this reference.

FIELD OF THE INVENTION

The field of art to which this invention relates is in the monitoring of certain parameters and transfer of such information to facilitate the diagnosis or therapeutic treatment for patients suffering from respiratory diseases, such as asthma or laryngopharyngeal reflux (LPR). More specifically, the present invention monitors the pH level of a patient's breath and provides data for determining the frequency and volume of a therapeutic dose to be administered to the patients' airways.

BACKGROUND OF THE INVENTION

Recently, it has been reported that the monitoring of acidity or pH of a patient's breath could help physicians in estimating the degree of air passage inflammation, now considered a key contributor to asthma, LPR and other respiratory conditions. Asthma is characterized by symptoms of wheezing, coughing, chest tightness, and shortness of breath. Manifestations include constriction (the tightening of the muscles around the airways) and inflammation (the swelling and irritation of the airways) that can be triggered through exposure to smoking, dust mites, pets, activity, cold, infection, weather, pollen, etc.

A clinical study of people with chronic obstructive pulmonary disease (COPD), bronchiectasis and asthma demonstrated more acidic levels in COPD and bronchiectasis patients, which is indicative of the chronic inflammation that these patients experience. This study also observed an increased acidic level measured from the breath of patients suffering from moderate asthma when compared to mild forms of the disease. It was also found that the asthmatics' breath was much more acidic during asthma attacks, but normalized after anti-inflammatory medication was administered.

This data suggests that the monitoring of an asthmatic's breath for pH might be an effective way to measure the degree of inflammation in the air passages. Furthermore, this data suggests that close monitoring of an asthmatic's breath pH could lead to prompt and effective treatment, minimizing the occurrence of asthma attacks and providing overall better asthma management.

It is estimated that 18-26 million people in the United Stated suffer from asthmatic conditions ranking this disease as the $8^{th}$ worst chronic condition in the US. It is also believed that over 5.6 million of these asthma sufferers are under the age of 18.

Studies have also shown that gastroesophageal reflux (GER) affects approximately 40% of the US adult population and that 60-80 percent of all asthma patients have GER. Gastro-esophageal reflux is a condition in which gastric acid refluxes from the stomach and into the esophagus. Frequent reflux episodes may result in a potentially severe problem known as gastroesophageal reflux disease (GERD). GER is the most common cause of dyspepsia or heartburn. GER can also manifest in the micro-aspiration of acid from the esophagus into the airway and lungs, damaging tissue, and causing irritation of the vagus nerve. This irritation of the vagus nerve, which is common to both the esophagus and the bronchial tree, can cause constriction of the airway. Acid reflux above the lower esophageal sphincter can cause anatomical damage and is linked to sleep disordered breathing. It has also been found that bronchial dilator drugs can relax the lower esophageal sphincter and trigger GERD induced asthmatic conditions. Sleep apnea has also been found to trigger reflux events. Testing for GER and the diagnosis of GERD are typically accomplished by measuring pH with catheter based devices.

These current pH monitoring methods suffer from the following drawbacks: 1) the current method requires an invasive procedure to place a pH measurement catheter or implanted pH measurement capsule in the patient's esophagus, 2) the procedure is not well tolerated by some patients, 3) the catheter or capsule placement must be performed by a physician, 4) the capsule cannot be placed above the Upper Esophageal Sphincter (UES) to measure airway pH, and 5) there are no defined standards for evaluation of pH above the UES.

Accordingly, there is a need in this art for a novel, pH diagnostic and monitoring system with electronic or wireless communication linked to a processing receiver that can also be used to activate a therapeutic nebulizer/atomizer/humidifier for treating asthmatic or other respiratory conditions.

SUMMARY OF THE INVENTION

The present invention pertains to an invention for monitoring the pH level of a patient's breath in a specially designed mask or sensor module that provides a means for transferring this data to a processing receiver for diagnosing disease abnormalities and determining the frequency and volume of a therapeutic dose to be administered to a patient, typically with a respiratory condition such as asthma. Monitoring of a patient's breath chemistry is provided by a system that includes a miniaturized pH sensor, provides for real-time monitoring of patient airway pH values, and utilizes solid state cooling to precipitate moisture from a patient's breath.

The specially designed respiratory mask or sensor module is mounted with a miniaturized pH sensor and data transfer means, e.g. direct wiring or by providing a transmitter with an antenna for wireless transferring of the pH data to a processing receiver. The temperature of the pH sensor is lowered below the dew point of the exhaled patient breath by a solid-state Peltier junction engaged on one side to a heat sink. A thermocouple is provided to monitor the temperature of the sensor for more accurate pH calculations. Keeping the sensor temperature below the dew point will cause the patient's exhaled breath to condense as a liquid in close proximity to the surface of the sensor. It is commonly known that monitoring of pH is significantly more accurate if measuring in a condensed liquid. A transmitter with an antenna transfers the observed pH data by employing one of many wireless methods, such as radio-frequency (RF) energy. Alternately, the transfer of observed pH data is accomplished by direct wire methods.

The pH data is transferred or updated at specific intervals, which can be varied according to the patient's needs, to the processing receiver that is engaged to the treatment apparatus. The processing receiver computes and diagnoses the breath chemistry data and determines at what frequency the treatment apparatus should be activated.

The present invention mask or sensor module may also be fitted with a means to remove the condensed liquid through an exhaust port or a connected pneumatic hose to remove unnecessary and accumulated breath condensate.

These and other features, aspects and advantages of the present invention will become better understood with reference to the following descriptions and claims.

DESCRIPTION OF THE PREFERRED EMBODIMENTS

The present invention provides a system and method for monitoring physiological parameters from a patient's exhaled breath and communicates this information to a processing computer/receiver that diagnoses, stores, or displays the information. The system can use computational instructions to activate and de-activate an electrically connected treatment nebulizer/atomizer/humidifier device, and can be integrated with a continuous positive airway pressure (CPAP) device.

Figure 1:
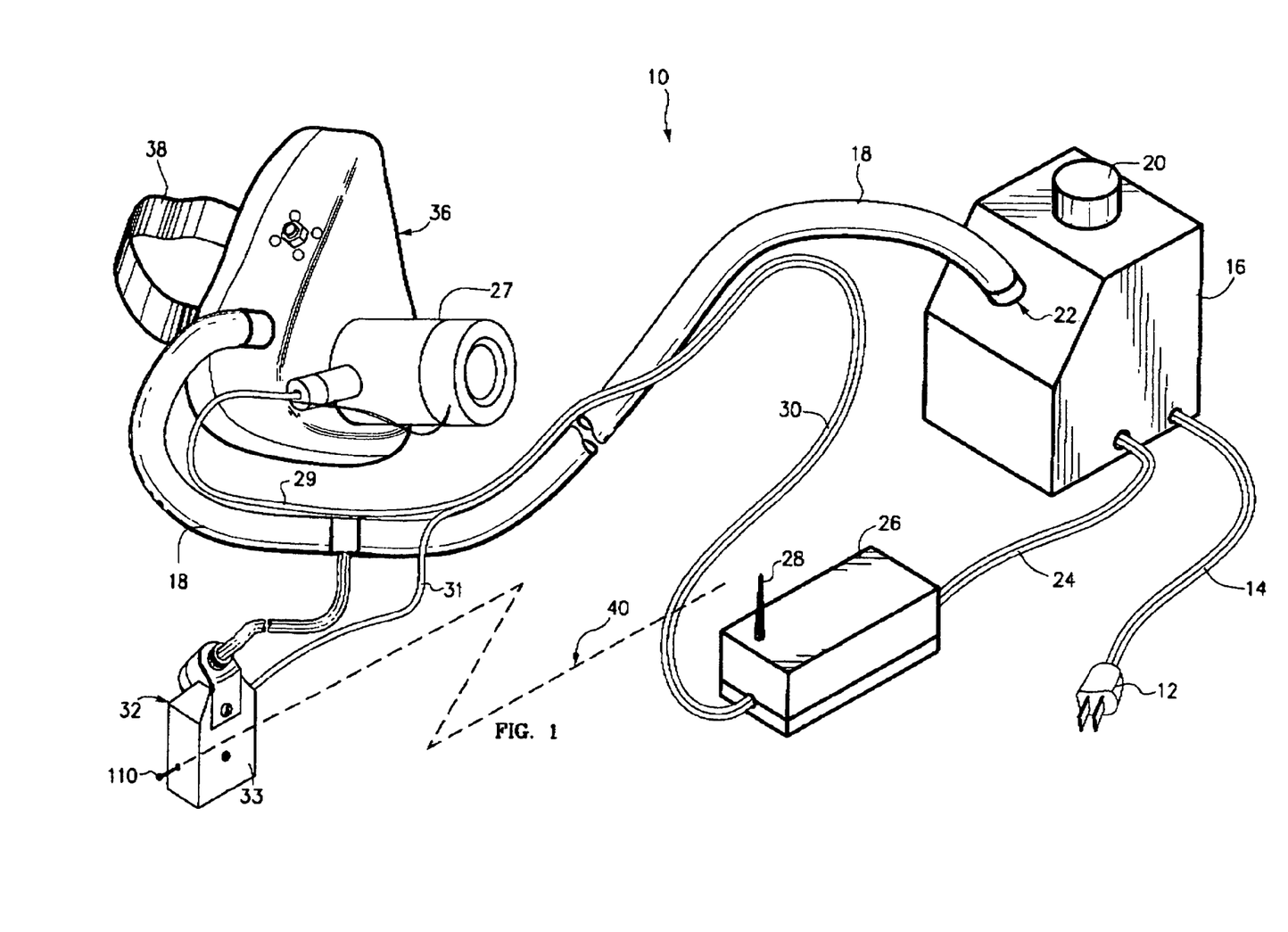
FIG. 1 is a perspective representation of the present invention systems, showing the various components of the system, including a mask apparatus fitted with a heat sink and pH sensing means, an optional continuous positive airway pressure (CPAP) device connected to the mask type apparatus, a processing receiver electrically connected to said mask apparatus, and a nebulizer/atomizer/humidifier device electrically connected to the processing receiver.

FIG. 1 illustrates that the present invention consisting of a system 10 comprised of several components. As shown in the Figure, a typical mask apparatus 36 is fitted with a securing strap or typical headgear apparatus 38. The mask configuration is only one embodiment contemplated by the Applicants. The present invention can perform in a mask-less configuration, with the other embodiments consisting of mounting the sensor assembly to a headband or other securing means that suspends the sensor assembly in the path of a patient's exhaled breath. If the example mask apparatus 36 is employed, it is generally fabricated from a polymeric and/or silicone material and configured to fit over a patient's nose, or nose and mouth, to assist in breathing conditions. The securing strap 38 is made from a flexible material and is positioned around the patient's head such that the mask substantially engages the patient's face and mouth area, minimizing ambient air from entering the boundaries of the mask. It is contemplated by the Applicants that other mask configurations, including a sensor module without mask, or mask-less configurations, and different positions of the components of the present invention, can still achieve the goal of monitoring, diagnosing and treating respiratory and medical conditions in patients.

Shown attached to the front of the mask apparatus 36 is a housing 27 that contains the components necessary for condensing the patient's breath and monitoring certain chemical parameters. The housing 27 can be machined or molded from a variety of polymeric materials including polyethylene, polypropylene, polyvinyl chloride, polystyrene, ABS, nylon, delrin, or polyethylene terephthalate (PET), or from metallic materials, such as aluminum or other biocompatible metallic alloys.

The mask apparatus 36 may be connected to the exit port 22 of a CPAP device 16 by means of a pneumatic hose 18. The hose can be manufactured from a variety of materials, including polymers such as polyethylene, polypropylene, polyvinyl chloride or silicone. The material used for the hose should be resistant to water and acidic environments, and should not interfere or interact with any medicaments employed in the present invention. CPAP air exits port 22 and travels along the length of the pneumatic host 18 to the internal sampling cavity created by the general mask apparatus covering the patient's face. The CPAP device has a control means 20 for increasing and decreasing the volume of air generated by the apparatus and the output of an optional humidification device. The CPAP device and humidifier are powered by an electrical source such as a standard plug 12 and cable 14.

Shown connected to the body 27 is an electrical wire 29 that communicates with a processing receiver 26.

Electrical wire 29 is typical in that the internal core comprises an electrically conductive metallic material and is encased by a nonconductive jacket. Processing receiver 26 is connected to the CPAP device 16 by an electrical wire 24 for controlling the activation of air generated by the CPAP device 16 and transferred to the typical mask apparatus 36. Also, an electrical connection by means of a wire 31 to the processing receiver 26 is a treatment nebulizer/atomizer/humidifier device 32. As an alternate method, a wireless means 40 can be utilized instead to communicate between the processing receiver 26 with an antenna 28 to the treatment nebulizer/atomizer/humidifier device 32. Although not shown in detail in FIG. 1, a wireless means also can be employed to communicate between the typical mask apparatus 36 and the processing receiver 26. In addition, a wireless means also can be employed to communicate between the processing receiver 26 and the CPAP device 16. As appreciated by those skilled in the art, wireless means for communicating between various components can be accomplished using radio frequency waves, microwaves, ultrasonic waves, or light optics.

The treatment nebulizer/atomizer/humidifier device 32 is pneumatically connected to hose 18 at some point along its length between the CPAP device 16 and the typical mask apparatus 36. The treatment nebulizer/atomizer/humidifier device 32 has a medicament storage chamber 33 where various types of therapeutic medicaments can be delivered to the pneumatic system and to the patient at intervals commanded by the processing receiver 26. If necessary, a scavenger can be added to the mask air outlet to remove excess medicament if it is inappropriate to vent the medicament into the room air.

Figure 2:
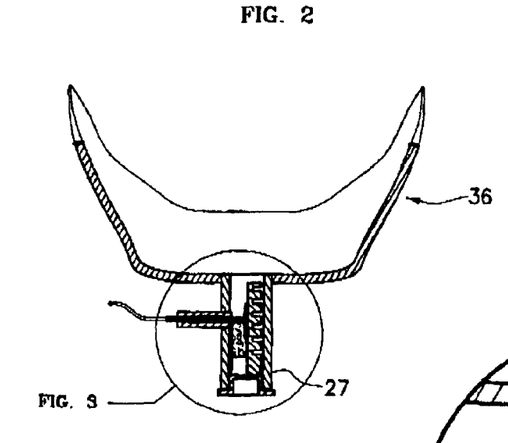
FIG. 2 is a sectional top view of the mask apparatus demonstrating in more detail of the orientation and components of the mask and the pH sensing apparatus.

FIG. 2 illustrates a sectional top view of the mask apparatus demonstrating in more detail the orientation and components of the mask 36, the condensing/monitoring body 27 and the pH sensing means 46.

Figure 3:
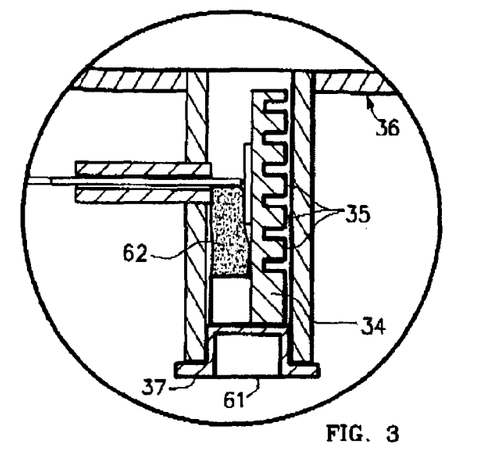
FIG. 3 is an enlarged sectional view taken from FIG. 2 demonstrating the general location of the pH sensor, internal heat sink, Peltier junction, absorption means, and one-way valve.

FIG. 3 is an enlarged sectional view taken from FIG. 2 demonstrating the general location of the pH sensor 46, internal heat sink 34, Peltier junction 50, absorption means 62, and one-way exhaust valve 61. The internal heat sink is fabricated generally from materials that have good heat conduction properties, such as certain metallic elements and alloys. Some candidates are aluminum, copper, silver and gold. The Peltier junction 50 is engaged to a polymer film 63 (shown in more detail in FIG. 4) and reduces the temperature of the film 63 to facilitate the condensation of breath into a liquid that pools on the surface of the film 63 and becomes exposed to the pH sensor 46.

Figure 4:
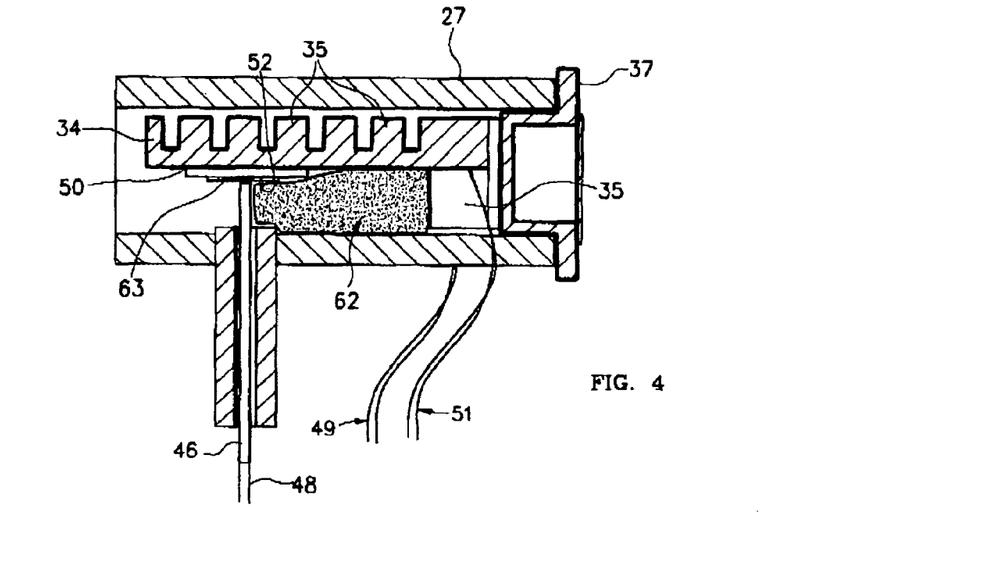
FIG. 4 is a sectional side view taken from FIG. 2 demonstrating in more detail the relative locations of the heat sink, Peltier junction, absorption means, condensing film, and pH sensor.

FIG. 4 is a sectional side view taken from FIG. 2 demonstrating in more detail the relative locations of the internal heat sink 34 with fins 35, Peltier junction 50, absorption means 62, condensing film 63, thermocouple 52 and pH sensor 46. The heat sink 34 is fitted with fins 35 to increase the surface area of the heat sink 34 to dispense heat generated by the system. As shown in this figure, Peltier junction 50 engages the back of heat sink 34. The Peltier junction 50 is connected by wires 51 to a DC power source, such as a battery (not shown) that generally is in the range of 0.2 to 12 volts. The Peltier junction 50 functions as a heat pump, removing heat from the condensing film 63, thereby reducing its relative temperature, and transferring the heat to the heat sink 34 and fins 35 that dissipates it into the environment (and a portion of the absorption means). The net effect of this operation is that the temperature of the high surface-tension film 63, engaged to the cool side of the Peltier junction, is lower than the ambient dew point. Breath condenses on the film 63 forming a pool of liquefied breath that is retained on the surface. The film 63 is generally composed of a polymer material having high surface-tension properties, one example being a mylar-based material.

The pH sensor 46, shown here as a tubular design, is comprised from a metallic antimony or similar alloy that is fitted with a plurality of wires or wireless means to communicate the analog pH information monitored by the sensor to a processing receiver 26. Similarly, the thermocouple 52 is fabricated from standard metallic components and is fitted with a plurality of wires or wireless means to communicate the analog temperature information monitored by the thermocouple to the processing receiver 26. The pH sensor 46 is positioned such that its terminal end is mounted in close proximity to the surface of the film 63 such that it gets exposed to a sample of breath condensed on the film 63. The thermocouple 52 is shown also residing near the terminal end of the sensor 46. The Applicant contemplates that other mounting positions for the thermocouple 52 and pH sensor 46 can be employed without sacrificing any performance.

Electronic communication from the pH sensor wires 48 and the thermocouple wires 49 that are further connected to a wire or wireless means for communication to the processing receiver 26. In the case of a wireless means, wires 48 and 49 would terminate in an antenna (not shown) and communicate with an antenna associated with the processing receiver 26.

An absorption means or pad 62, generally constructed from an expanded open-cell material such as certain types of cellulose or urethanes, is mounted with one end in close proximity to a portion of film 63 and the other end in close proximity with the heat sink 34. The absorption means or pad 62 has the capability to continuously draw or extract, from the surface of film 63, some of the liquefied breath sample into its open-cell structure. The portion of absorption means or pad 62 in contact with the heat sink 34 causes its temperature to increase. The increased temperature functions to return the breath condensate back into a gaseous state thereby promoting evaporation of the sampled breath. Pulses of non-condensed breath are forced over fins 35 of the heat sink 34 as well as through the open cell structure of the absorption means or pad 62. Mounted at the terminal end of body 27 is a one-way exhaust valve 61 fitted within a cap structure 37. Exiting out the one-way valve 61, either into the environment or vented to an appropriate location, is the non-condensed gaseous breath.

Figure 5:
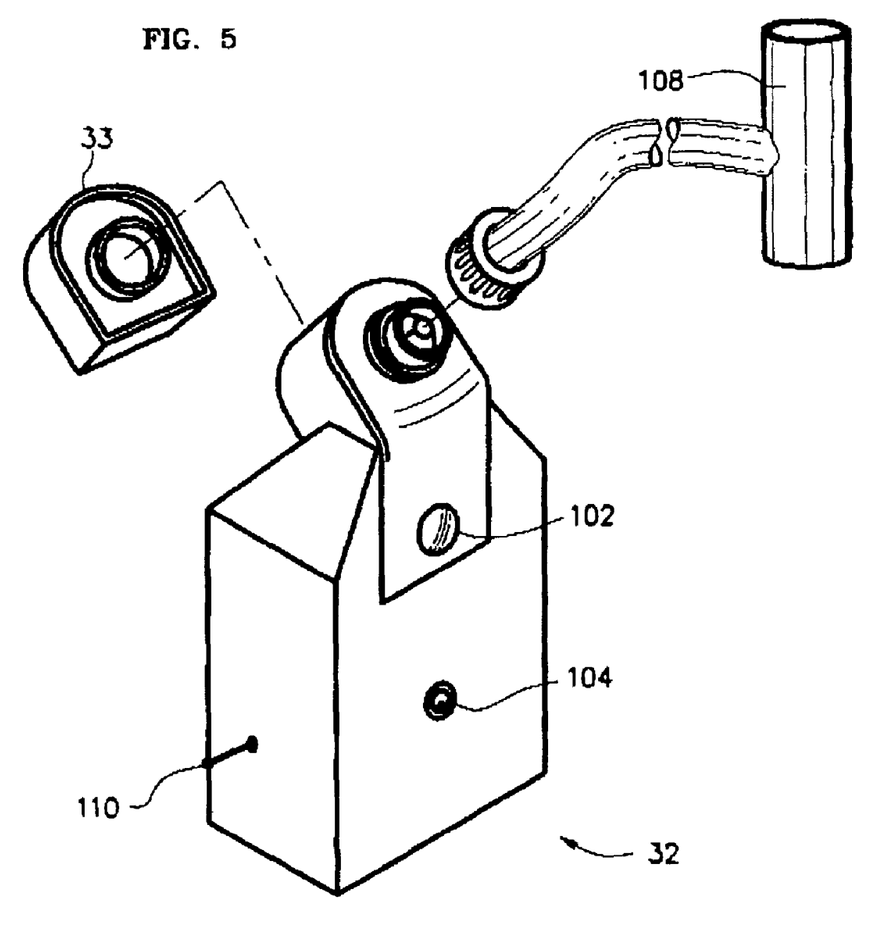
FIG. 5 is a schematic representation of the treatment nebulizer/atomizer/humidifier device, demonstrating a base unit having an on/off switch, operating lights, a medicament storage container, and interconnection for attaching the pneumatic hose.
Figure 6:
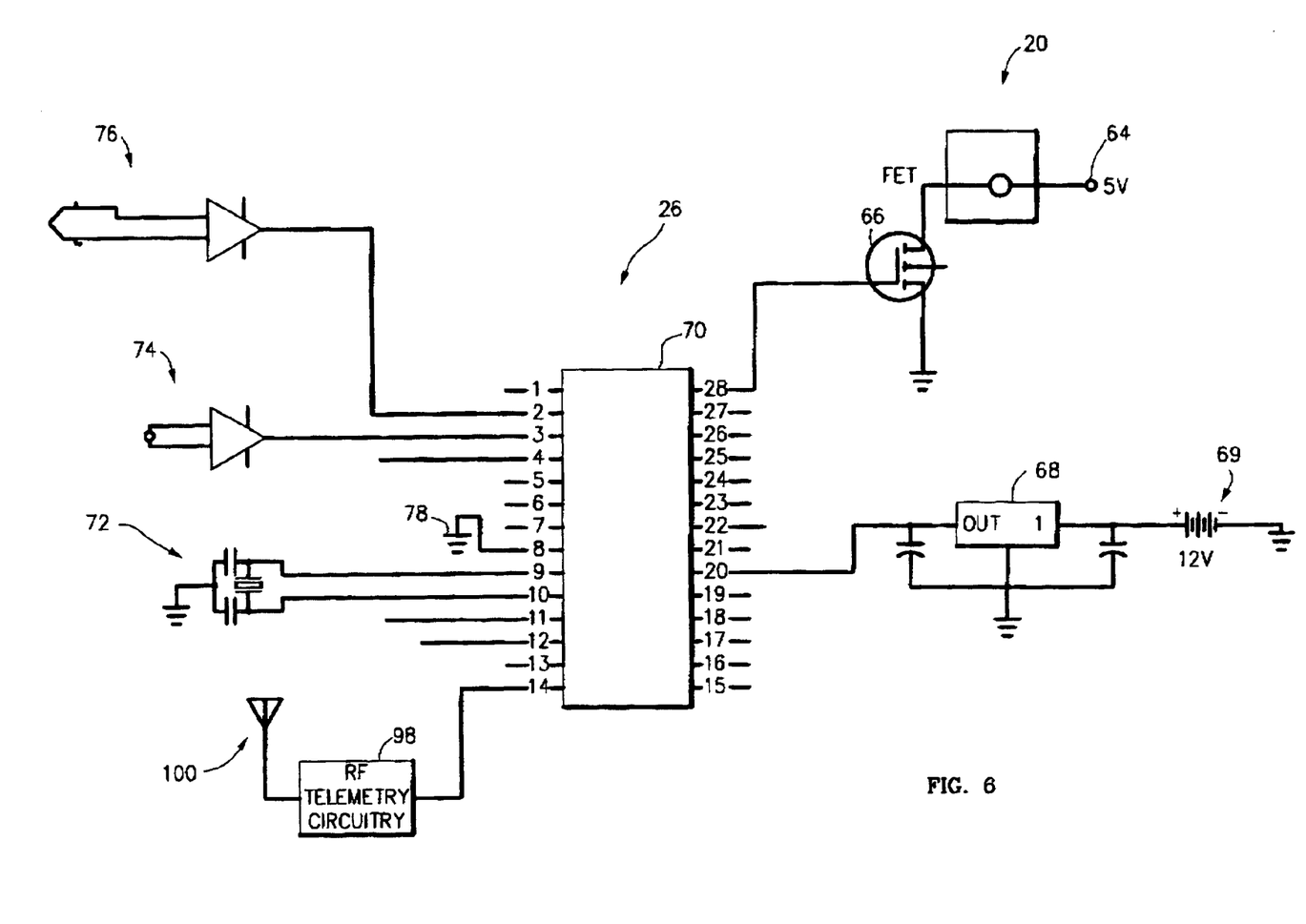
FIG. 6 is an electrical schematic of the general components in the processing receiver.

FIG. 5 is a schematic representation of the treatment nebulizer/atomizer/humidifier device 32, demonstrating a base unit having an on/off switch 102, operating lights 104, a medicament chamber 33, and interconnection 108 for attaching to the pneumatic hose 18. The treatment nebulizer/atomizer/humidifier device 32 has an outer shell surrounding various mechanical and electrical components that function to deliver the therapeutic dose. The shell can be made of a variety of materials, including plastics such as polyethylene, polystyrene, ABS, nylon, delrin, or polyethylene terephthalate (PET). The treatment nebulizer/atomizer/humidifier device 32 communicates with the processing receiver by direct wiring (not shown) or by use of wireless means employing an antenna means 110. The base unit and various components of the treatment nebulizer/atomizer/humidifier can be fabricated from polymeric or metallic materials. Operating light 104 can consist of LED, LCD, fluorescent, or halide or other means to communicate such conditions, as on/off, medicament chamber empty, etc. Also, the Applicant contemplates that a plurality of operating lights can be employed having different functions. The art associated with atomization of particles and humidification processes are known in the art. Many commercially available units can satisfy the basic requirements for the treatment nebulizer/atomizer/humidifier device 32. One such device is the MicroAir portable ultrasonic nebulizer manufactured by Omron Healthcare, Inc. of Vernon Hills, Ill. This device can be modified or fabricated so that 1) it can be remotely activated by the processing receiver 26, and 2) adapted to connect to the pneumatic tube by an appropriate connection 108 as shown in FIG. 5.

The medicament chamber 33 can contain liquid, gaseous or powdered therapeutics that the treatment nebulizer/atomizer/humidifier device 32 is designed to administer to the pneumatic system upon instructions from the processing receiver 26. It is contemplated that the medicament chamber 33 could include a plurality of medicaments in various compartments in the medicament chamber 33. It is also contemplated that treatment nebulizer/atomizer/humidifier device 32 can select to administer one or more, or in a combination, multiple medicaments stored in the medicament chamber 33. Either a continuous method or, to conserve medicine, a pulsed method corresponding with each breath detected by conventional means can be employed by the present invention.

FIG. 6 is a simplified electrical schematic of the general components in the processing receiver 26. In the center is the microprocessor 70 that processes the information supplied by the thermocouple and sensor and use internal instructions to control other devices. The microprocessor has an EEPROM memory section that allows for specific programming to be incorporated as processing instructions. Furthermore, the microprocessor must have the capability to convert analog signals into digital information for decoding and processing. An example of a microprocessor that could be used in the processing receiver 26 is the PIC16F876 28-pin 8-Bin CMOS FLASH micro-controllers manufactured by Microchip Technology, Inc. This particular microprocessor has a 128K EEPROM Data memory bank for flash memory of specific instructions and utilizes a 35-word instruction set. It also has five 10-bit Analog-to-Digital Inputs that are necessary for converting the information obtained from the pH sensor 46 and thermocouple 52 from its analog format into a digitized form for processing by the instruction sets of the microprocessor 70.

The microprocessor 70 includes a timing crystal 72 used for clocking operations and is connected to and energized by an approximate 12 volt power supply 69. Also included in the circuit is a power transistor 66 with an electrical connection to the nominal 12-volt power supply, a nominal 5-volt regulator 68, and a ground 78.

The sensor analog data that is communicated either through direct wiring or through a wireless means that is then amplified by a circuit 74 and connected to the microprocessor 70 through one of the analog-to-digital modules.

In addition, the thermocouple analog data that is communicated either through direct wiring or through a wireless means that is amplified by circuit 76 and connected to the microprocessor 70 through another one of the analog-to-digital modules.

In certain embodiments, the transmitted data can be recorded, compressed and stored as it is received using a memory chip set or memory circuit within the microprocessor (not shown). Subsequently, the data stored can be downloaded into an external data retrieval device, which can be a computer or other analysis machine.

Figure 7:
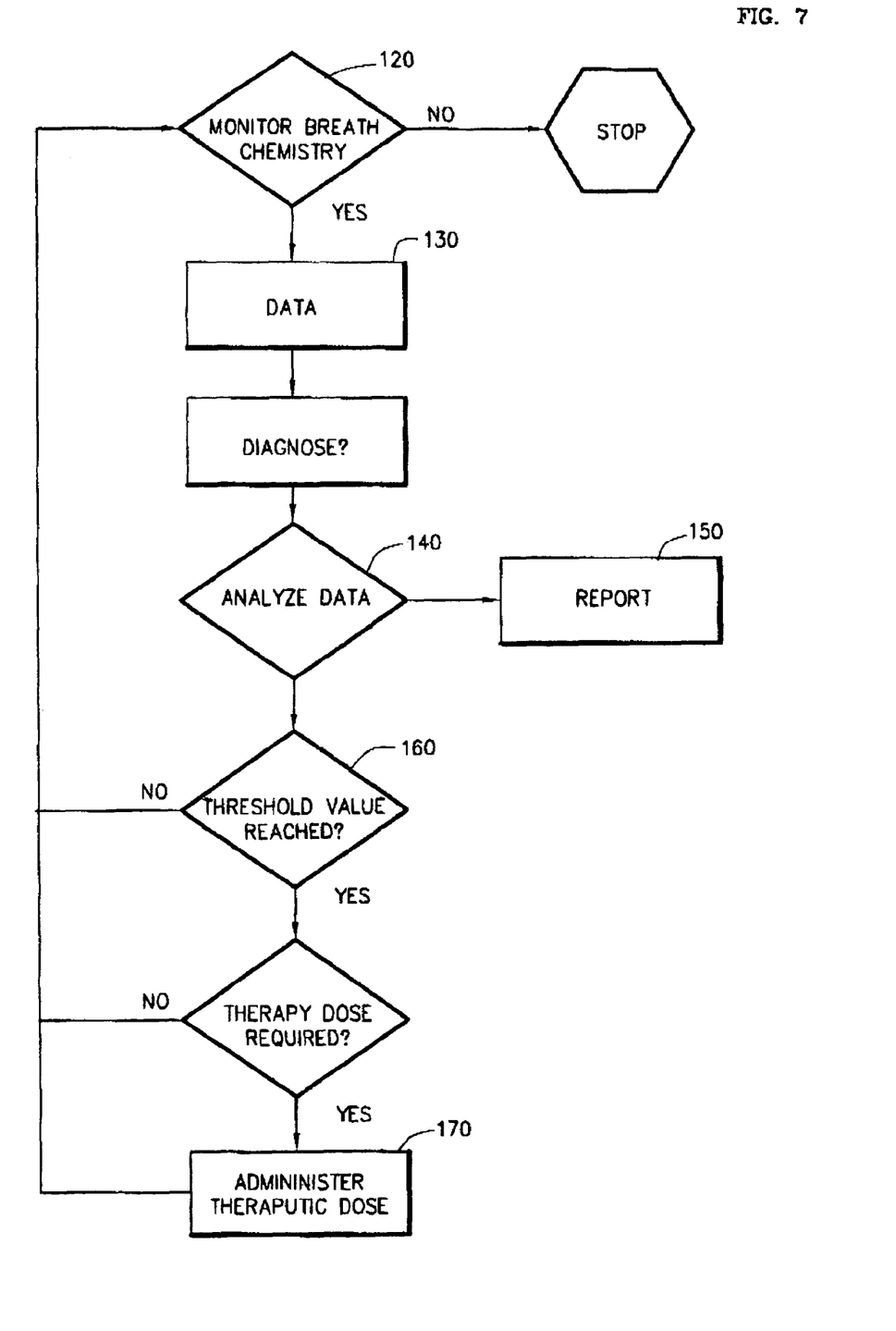
FIGS. 7 and 8 are flowcharts showing the sequential computational steps employed by the processing receiver.
Figure 8:
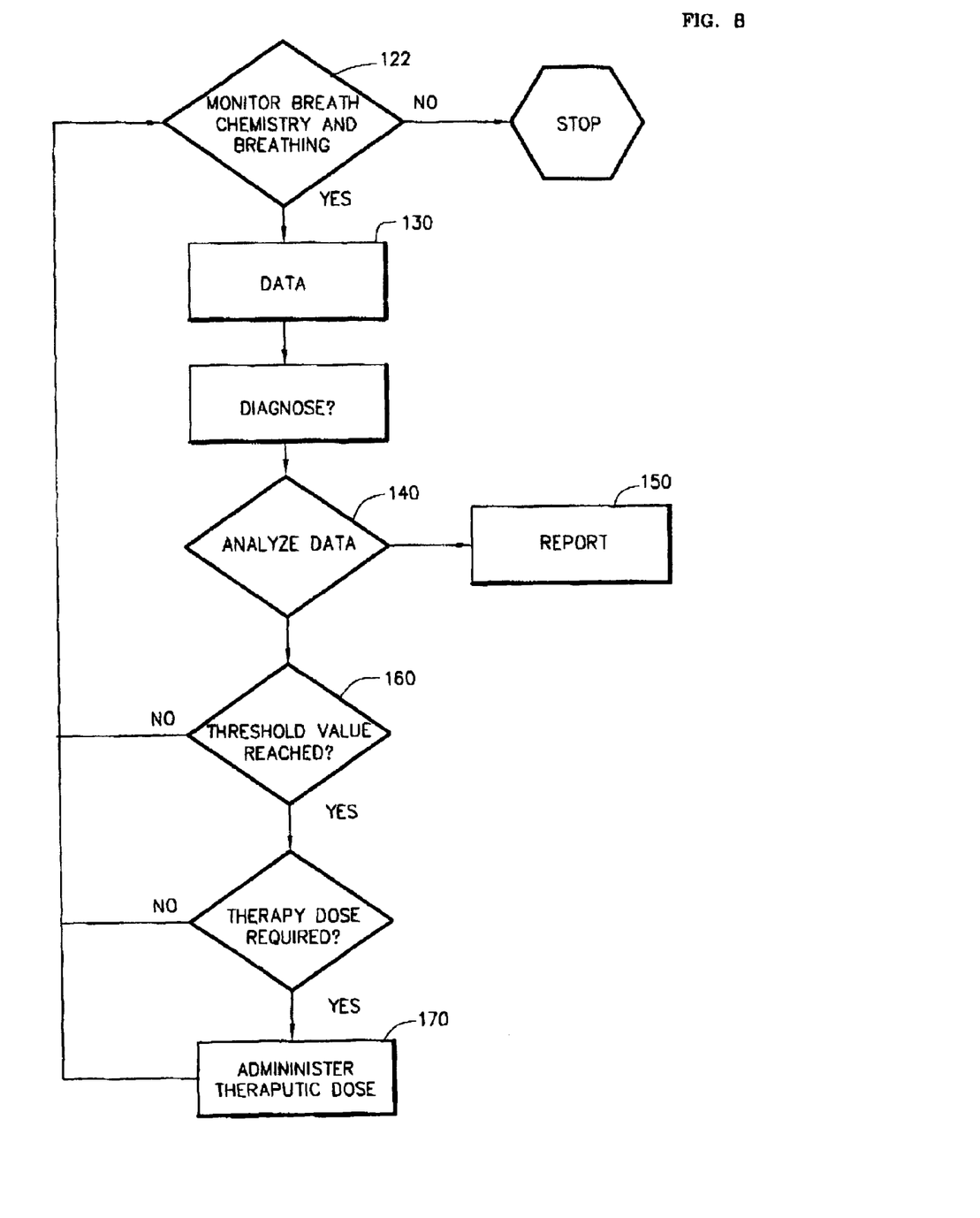

FIGS. 7 and 8 illustrate flowcharts showing the sequential computational steps employed by the processing receiver 26. As described above, the microprocessor 70 has an EEPROM memory section that allows for specific programming to be incorporated as processing instructions. The steps programmed in the microprocessor 70 are outlined in the flowcharts, starting with the 1) monitoring of breath chemistry 120 without CPAP support (FIG. 7) 2) the monitoring of breath chemistry and breathing rates (122) with CPAP support (FIG. 8). The analog information obtained from the sensor and the thermocouple is converted to digital information and transferred to the microprocessor. The microprocessor uses the thermocouple data to calculate an accurate pH level that is stored in a registry. Optionally, this data can be diagnosed by the microprocessor 70 to analyze and diagnose data 140 and stored in a memory bank whereby the microprocessor 70 can create diagnostic reports 150.

The stored data is then compared to a threshold value or range 160 programmed in the instruction set of the microprocessor 70. For example, if the pH level does not reach the threshold value, then no actions are performed and the instruction set loops back to read breath chemistry (FIG. 7) or breath chemistry and monitor breathing rates (FIG. 8). If the pH level reaches the threshold value, then the microprocessor 70 determines the appropriate therapy 170.

These computational steps can be continued over and over again to detect, record, analyze and administer the appropriate therapeutic regime to manage patients with certain respiratory conditions.

Figure 9:
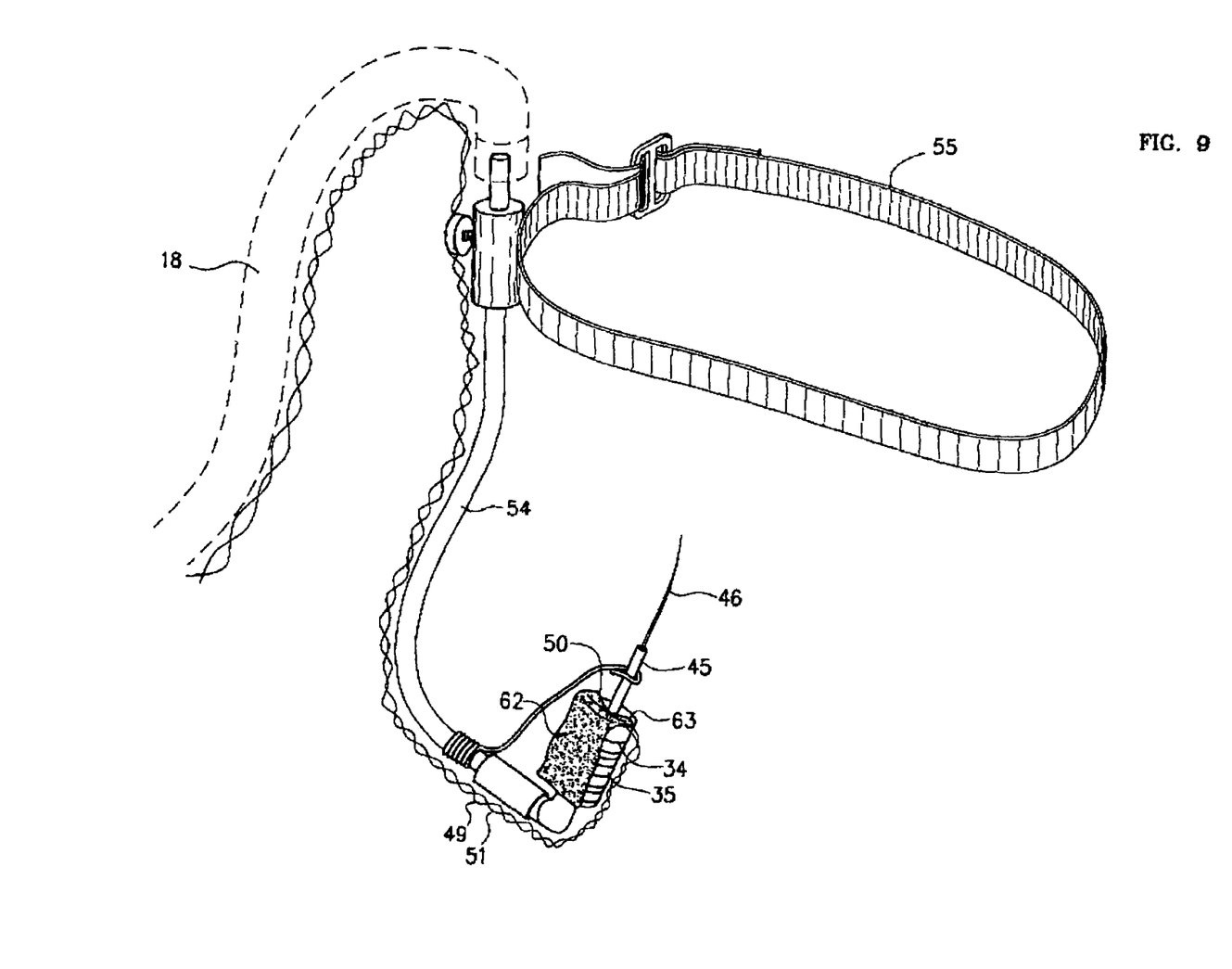
FIG. 9 is a perspective representation of another embodiment of the present invention systems, showing the various components of the system, including the heat sink/condensing means and pH sensing means suspended from a maskless apparatus to locate the present invention in the path of a patient's exhaled breath.

FIG. 9 is a perspective representation of another embodiment of the present invention, showing various components of the system, including the heat sink/condensing means and pH sensing means suspended from a mask-less apparatus to locate the present invention in the path of a patient's exhaled breath. Shown is an adjustable headband 55 designed to be worn around the head of a patient. Attached to various locations of the headband 55 is a suspension member 54. The other end of the suspension member 54 is attached to a heat sink assembly 34. Heat sink assembly 34 is fitted with fins 35 to increase the surface area of the heat sink 34 to dispense heat generated by the system. The suspension member 54 should be fabricated from a material that provides a stable platform for maintaining the position of sensor 46 in the path of a patient's exhaled breath yet also be adjustable for the various physical measurements of patients. A sensor body 45 is shown projecting outwardly from heat sink assembly 34 that provides support for a further projecting sensor 46. Also shown in FIG. 9 is a rigid support wire attached at one end to the suspension member 54 and on the other end to heat sink assembly 34. Draped along and in close proximity to a portion of the heat sink assembly 34 is absorption means or pad 62. The other end of absorption means or pad 62 is in contact with condensing film 63 for wicking liquefied breath into the open cell structure. Condensing film 63 is in close association with Peltier junction 50 and thermocouple 52 (with electrical connection 49) to provide temperature control. Peltier junction 50 engages a portion of heat sink 34 and is connected by wires 51 to a DC power source, such as a battery (not shown). The Peltier junction 50 functions as a heat pump, removing heat from the condensing film 63, thereby reducing its relative temperature, and transferring the heat to the heat sink 34 and fins 35 which function to dissipates the heat. The interaction of Peltier junction 50 with the condensing film 63 condenses a patient breath as disclosed with the other embodiments.

It is also anticipated by the Applicants that the present invention diagnostic means will examine the pH waveform patterns produced to diagnose diseases.

The present invention will: 1) Monitor; 2) Diagnose; 3) Treat a respiratory disease, with and without CPAP therapy.

While the invention has been described in detail and with reference to specific embodiment thereof, it will be apparent to one skilled in the art that various changes and modifications can be made therein without departing from the spirit and scope thereof.

We claim:

1. A system for monitoring a medical condition comprising:
   a film
   an apparatus that condenses a sample of an individual's breath on said film;
   a sensor in close proximity to said film, said sensor positioned such that it contacts said condensed sample of the individual's breath when the condensed sample is present;
   a processing receiver; and
   said sensor in real-time communication with said receiver.

2. The system as recited in claim 1, wherein said apparatus is a general mask or another device for directing the patients' breath towards said film.

3. The system as recited in claim 1, wherein said sensor is designed to monitor pH.

4. The system as recited in claim 1, wherein said medical condition is a respiratory condition, such as asthma, gastro-esophageal reflux or laryngo-pharyngeal reflux.

5. The system as recited in claim 1, wherein said communication is accomplished by a plurality of wires.

6. The system as recited in claim 1, wherein said communication is accomplished by a wireless means.

7. The system as recited in claim 1, wherein said apparatus has a means to continuously circulate and replace the sample of liquefied breath with a fresh sample of liquefied condensed breath.

8. The system as recited in claim 1, wherein said apparatus has a means to monitor the condensate temperature on said film.

9. A system for monitoring and diagnosing a medical condition comprising:
a film
an apparatus that condenses a sample of an individual's breath on said film;
a sensor in close proximity to said film, said sensor positioned such that it contacts said condensed sample of the individual's breath when the condensed sample is present;
a processing receiver;
said sensor in real-time communication with said receiver; and
said processing receiver processing said information for determining various diagnoses.

10. The system as recited in claim 9, wherein said apparatus is a general mask or another mask-less device for directing the patient's breath in close proximity to said sensor.

11. The system as recited in claim 9, wherein said medical condition is a respiratory condition.

12. The system as recited in claim 9, wherein said communication is accomplished by a plurality of wires.

13. The system as recited in claim 9, wherein said communication is accomplished by a wireless means.

14. The system as recited in claim 9, wherein said sensor is designed to monitor pH.

15. The system as recited in claim 9, wherein said apparatus has a means to continuously circulate and replace the sample of liquefied breath with a fresh sample of liquefied condensed breath.

16. The system as recited in claim 9, wherein said apparatus has a means to monitor the condensate temperature on said film.

17. A system for monitoring, diagnosing, and treating a medical condition:
a film;
an apparatus that condenses a sample of an individual's breath on a film comprising;
a sensor in close proximity to said film, said sensor positioned such that it contacts said condensed sample of the individual's breath when the condensed sample is present;
a processing receiver;
said sensor in a first real-time communication with said receiver;
said processing receiver processing said information for determining various diagnoses and treatments; and
said processing receiver in a second communication with at least one treatment device to administer at least one therapeutic dose.

18. The system as recited in claim 17, wherein said apparatus is a general mask or another mask-less device for directing the patient's breath in close proximity to apparatus.

19. The system as recited in claim 17, wherein said medical condition is a respiratory condition, such as asthma or laryngopharyngeal reflux.

20. The system as recited in claim 17, wherein said first communication is accomplished by a plurality of wires.

21. The system as recited in claim 17, wherein said first communication is accomplished by a wireless means.

22. The system as recited in claim 17, wherein said second communication is accomplished by a plurality of wires.

23. The system as recited in claim 17, wherein said second communication is accomplished by a wireless means.

24. The system as recited in claim 17, wherein said sensor is designed to monitor pH.

25. The system as recited in claim 17, wherein said treatment is a biocompatible agent capable of neutralizing an acidic condition.

26. The system as recited in claim 17, wherein said treatment is sodium bicarbonate.

27. The system as recited in claim 17, further comprising a communication between said processing receiver and a nebulizer/atomizer/humidifier.

28. The system as recited in claim 17, further comprising a third communication between said processing receiver and a continuous positive airway pressure device.

29. An apparatus for monitoring breath chemistry comprising:
a sensor;
a film;
a solid-state cooling means, said cooling means in close proximity with said film;
said cooling means reducing the temperature of said sensor below the dew point of a patient's breath such that the patient's breath condenses into a liquid that condenses on the film; and
said sensor position such that it is immersed in said liquefied breath on said film when the liquefied breath is present on the film.

30. An apparatus as recited in claim 29, further comprising a means to expel and replenish said collection pool with fresh liquefied patient's breath condensate.

31. The system as recited in claim 29, wherein said apparatus has a means to monitor the condensate temperature on said film.

* * * * *